United States Patent [19]

Arden

[11] Patent Number: 5,187,507
[45] Date of Patent: Feb. 16, 1993

[54] METHOD OF AND APPARATUS FOR DIAGNOSING PERIPHERAL FIELD DEFECTS AND OTHER PERIPHERAL RETINAL DAMAGE

[75] Inventor: Geoffrey B. Arden, London, England

[73] Assignee: The Institute of Opthalmology, London, England

[21] Appl. No.: 663,012

[22] Filed: Mar. 1, 1991

[51] Int. Cl.⁵ .............................................. A61B 3/02
[52] U.S. Cl. .................................. 351/226; 351/222; 351/224; 351/243
[58] Field of Search ............... 351/211, 222, 224, 226, 351/243

[56]         References Cited
       U.S. PATENT DOCUMENTS
   4,550,990  11/1985  Trispel et al. .................... 351/222

Primary Examiner—Bruce Y. Arnold
Assistant Examiner—Hung Xuan Dang
Attorney, Agent, or Firm—Antonelli, Terry, Stout & Kraus

[57] ABSTRACT

A method of diagnosing glaucomatous field defects of particular use in diagnosing the early stages of glaucoma and ocular hypertension is disclosed. The method comprises displaying an image comprising an annulus of a first color on a background of a second color to the patient, the annulus having a gap in it at a variable position. The patient is asked to identify the location of the gap and the tonal contrast between the first color and the second color is varied to determined the color contrast sensitivity threshold of the patient. Also disclosed is an apparatus for performing the method.

13 Claims, 3 Drawing Sheets 17  19  21

METHOD OF AND APPARATUS FOR DIAGNOSING PERIPHERAL FIELD DEFECTS AND OTHER PERIPHERAL RETINAL DAMAGE

FIELD OF THE INVENTION

This invention relates to the detection of peripheral field defects and other peripheral retinal damage and in particular to the diagnosis of glaucoma and ocular hypertension and the identification of subjects with a high risk of developing glaucoma and other conditions in which peripheral retinal damage occurs.

BACKGROUND ART

While methods of diagnosis of eye disease depend to a considerable extent on determining abnormalities of vision, the patient's attention is in general confined to those parts of the images of the outside world which fall on a small central region of the light-sensitive retina, known as the fovea or macula. However, many diseases may start at random anywhere on the retina, and the patient is then unaware of any defect. The standard test of visual acuity depends upon foveal function, and is now recognized to be insufficient as a means of describing vision and its defects. Therefore, other pieces of equipment called generically perimeters have been devised to test function at all other points in the retina (known as the peripheral and paramacular retina). What these have in common is that the locus of a point or points in the retina in which function is altered are specified. To test vision with such equipment takes considerable time and it is difficult for the patient to cooperate.

DISCLOSURE OF INVENTION

The present invention is based upon the insight, that for many purposes, especially in screening for disease, the site of damage is unimportant, so long as the presence of some damage can be demonstrated, and that by dispensing with information about the precise site of a retinal lesion the speed and other aspects of diagnosis can be improved. Methods have been devised (a number of connected technical innovations, described later in this document) to embody this principle and it has been shown that diagnosis can be made more rapidly than by previous methods. The sensitivity (in detecting the earliest stage of the disease) is improved over other methods, and the ability to distinguish disease states from the range of the normal (known as selectivity) is also enhanced. This general claim is illustrated in respect to the eye disease known as glaucoma. The operation of the equipment can be modified to suit other diagnostic situations.

According to the present invention there is provided an apparatus for use in diagnosis of peripheral field defects or other peripheral retinal damage. The apparatus comprises:
  an image generator for generating an image comprising an annulus on a background, the annulus having an interruption in a selectable manner and being distinguished from said background by a distinction in a visually perceivable property; means connected to said image generator for changing the distinction between said annulus and background in a graded manner in that property; and
  a display for displaying the image.

The present invention also provides a method of diagnosing peripheral field defects or other peripheral retinal damage in humans. An image comprising an annulus on a background, is generated. The annulus has an interruption in a selectable manner and is distinguished from the background by a distinction in a visually perceivable property. The image is displayed to a patient and it is determined whether he or she can correctly determine the position of the interruption. The distinction between the annulus and the background is changed in a graded manner and the steps of generating and displaying the image and determining whether the patient can detect the interruption are repeated to determine thereby the sensitivity of said patient to said property.

The patient's threshold to a particular stimulus is the limit below which that stimulus ceases to be perceptible to the patient. This is measured by presenting a stimulus to the patient and reducing the possibility of distinguishing the stimulus, in a stimulus dimension proper to that stimulus, and to the condition for which the test is being carried out, until the patient cannot make distinctions about the presence or absence of that stimulus.

Where the property is colour the annulus is of a first colour and the background of a second; the first and second colours are preferably chosen so that they lie along a line of colour confusion for the patient; and are preferably of equal perceived luminosity.

Preferably the annulus has n acute angles and it is optionally circular. The image preferably also includes a fixation point in the centre of the annulus and the annulus is preferably of a size such that it has a radius of approximately 12.5 degrees in the extramacular field, occupying approximately 90 minutes of arc. A chin rest may be provided to assist the patient in maintaining the correct distance, preferably approximately 45 cm, from the displayed image.

The present invention will be further described hereinafter with reference to the following description of a preferred exemplary embodiment and the accompanying drawings, in which:

BEST MODE FOR CARRYING OUT THE INVENTION

Figure 1:
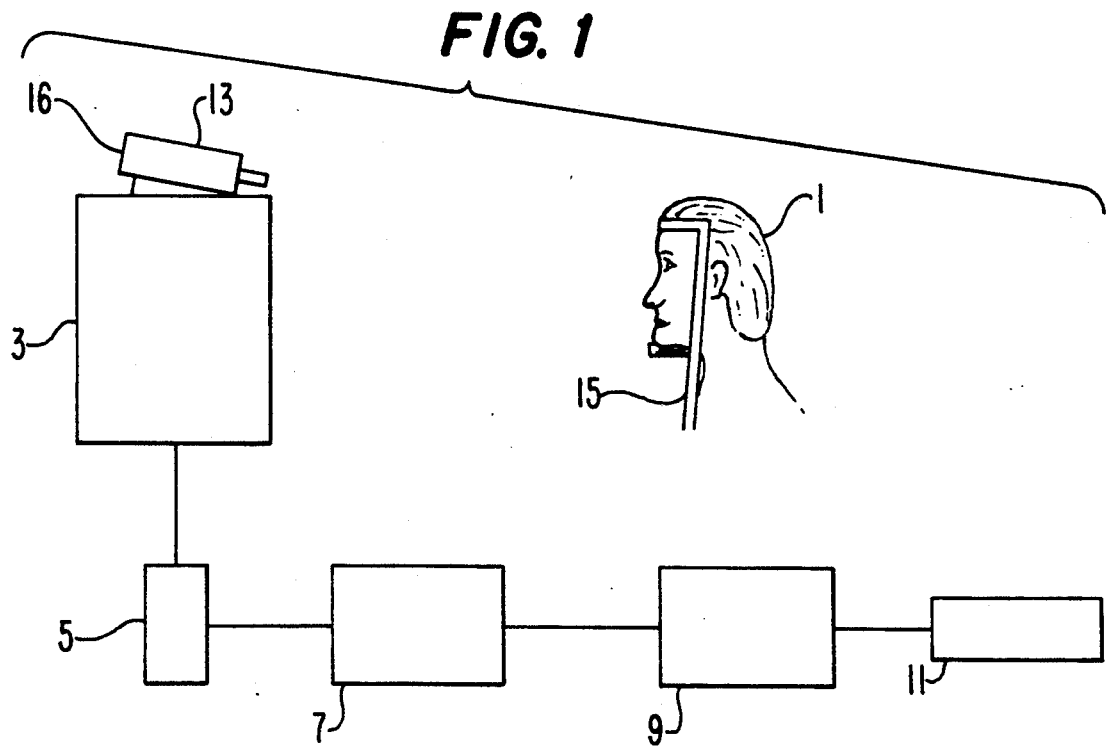
FIG. 1 is a schematic view of an apparatus according to the present invention.
Figure 2:
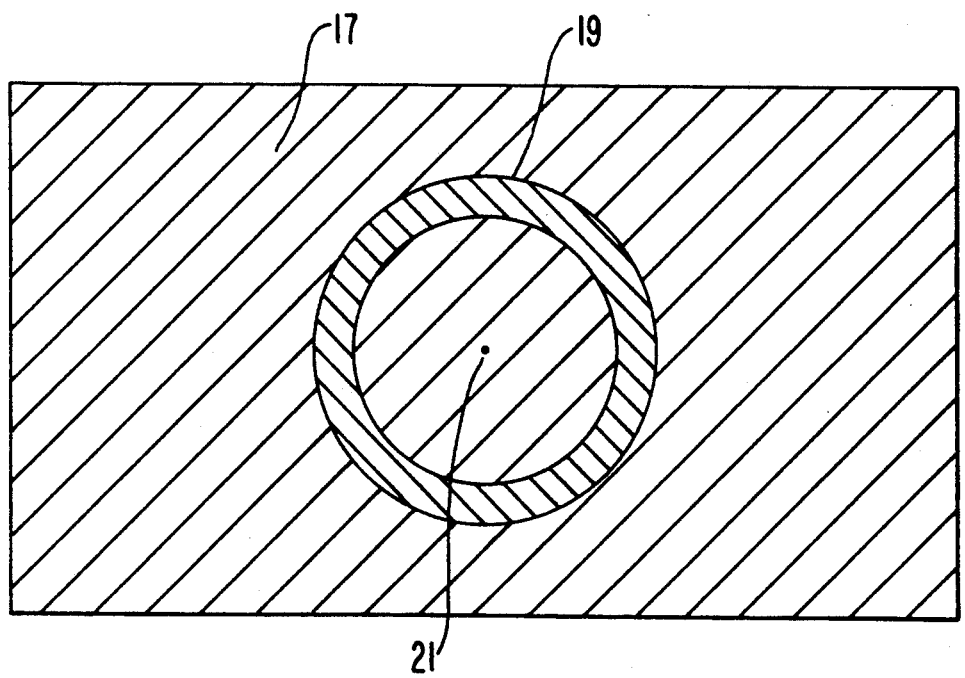
FIGS. 2 to 4 show images produced by the apparatus.
Figure 3:
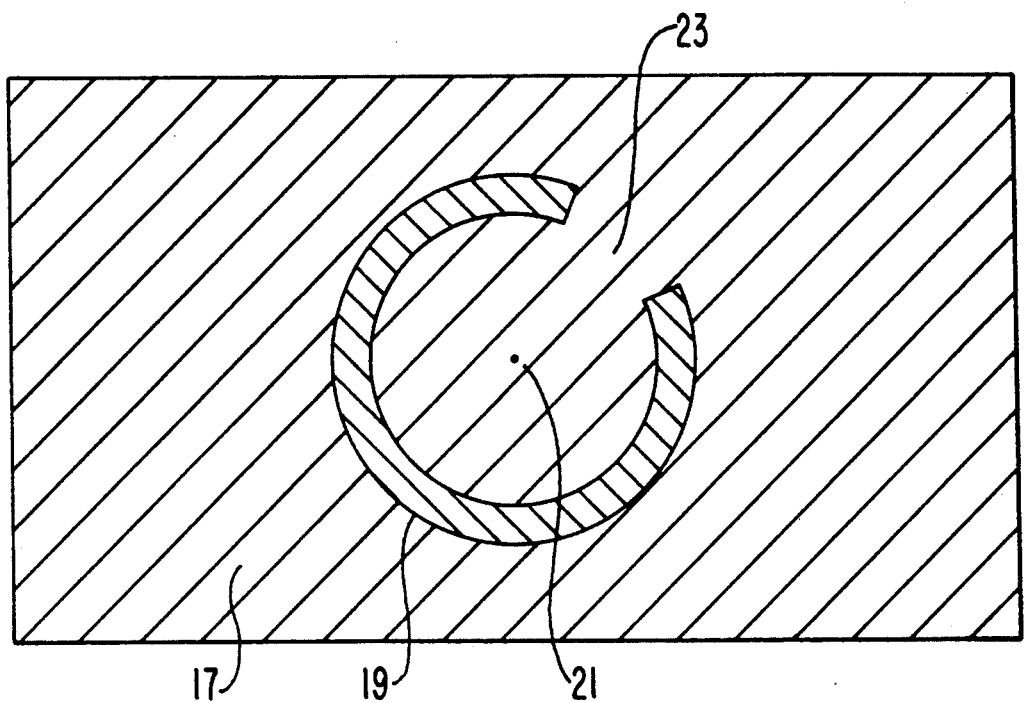
Figure 4:
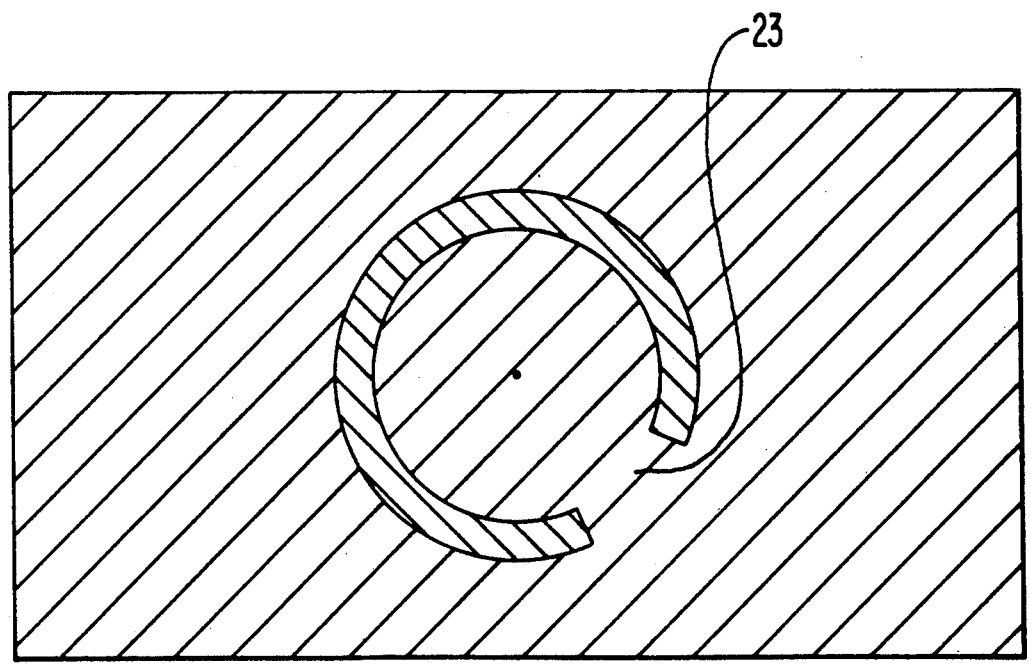

An apparatus embodying the present invention is shown in FIG. 1. The patient 1 is situated at a predetermined distance, in this case 45 cm, from the screen 3, which he/she observes. The screen 3 displays an image, examples of which are shown in FIGS. 2 to 4, which is generated by the image generator 7 under the control of the controller 9 to which data and commands can be input by the operator via the input means 11. The image generated by the image generation means 7 is filtered by the low pass filter 5 before display to soften the sharp edges of the displayed annulus. The image need not be an annulus, it need only be approximately circular and have both inner and outer borders.

In the preferred embodiment the image is generated by a personal computer with a high definition video graphics adapter and a high definition multisync colour monitor. The computer is supplied with the responses of the patent, e.g. via keyboard or a mouse, and conducts a "Modified Binary Search", discussed below, to find the patient's sensitivity. The display can also be calibrated to determine at what intensities various colours are perceived by the patient to be equiluminous. In order to calibrate the apparatus for the particular patient, the patient is first presented with a flickering red-green patch and adjusts the luminosity of the red and the green to produce minimum flicker sensation. The process is repeated for a flickering blue green patch and the results are used to calculate the colour confusion axes and the intensities which are perceived as equiluminous.

FIG. 2 shows the basic form of the image displayed on the display unit 3. The basic image comprises an annulus 19 on a background 17 with a fixation spot 21 at the centre of the annulus 19. The annulus and background are of contrasting colours lying on a tritan colour confusion axis and are of equal perceived luminosity.

In the test the patient fixates on the fixation spot at the centre of the annulus and a television camera 16 is connected to a television screen visible to the ophthalmologist which enables him to detect any change in fixation.

At the beginning of the test high and low bounds for the colour contrast i.e. separation in colour space as defined by the Commission Internationale de l'Eclairage are set and placed on stacks. The contrast of the display is set to midway between the two bounds. A 45° portion of the ring in a quadrant 23 is removed at random such as illustrated in FIGS. 3 and 4 and the patient is asked to identify where the break is. If the patient gives the correct answer then the contrast of the display is pushed onto the upper bound stack while if an incorrect answer is given the display contrast is pushed onto the lower bound stack. The contrast of the display is then adjusted to midway between the values on the top of the stacks and the ring again displayed with a segment missing such as illustrated in FIGS. 3 and 4. If more than two correct or incorrect results ar obtained in succession the lowest stack level of this "binary search" is popped and becomes the new bound. The system thus rapidly converges on the patient's threshold while at the same time taking account of the fact that the patient may give the correct answer even when he or she has not correctly located the break.

It is important that the annulus has no sharply defined edges or luminosity variations which might assist the patient in identifying the location of the break. The annulus is thus spatially filtered by a low pas filter before display to ensure a smooth transition from the colour of the background to the colour of the annulus.

Figure 5:
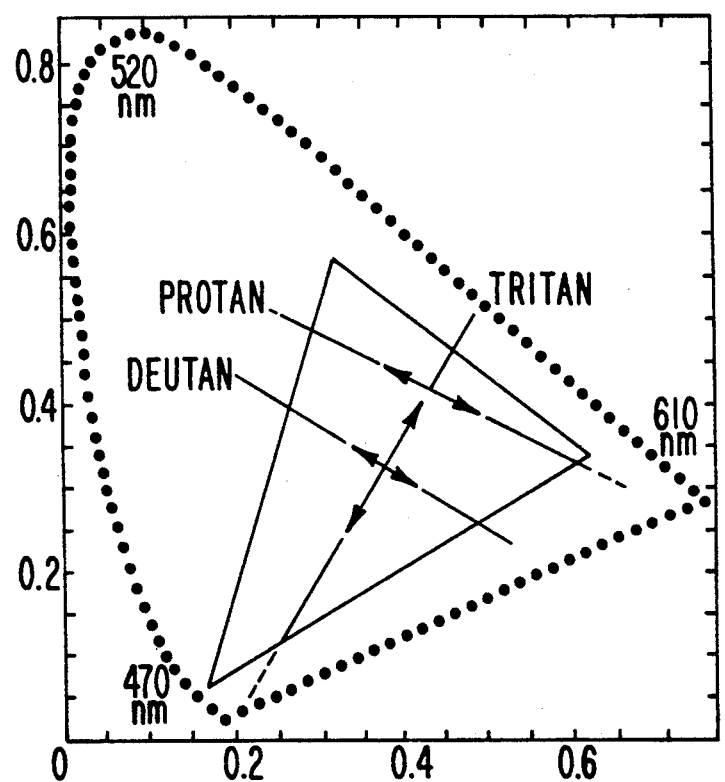
FIG. 5 shows the Protan, Deutan and Tritan colour confusion lines on a CIE chromaticity diagram.

FIG. 5 shows the protan, deutan and tritan colour confusion axes plotted on a standard Commission Internationale de l'Eclairage chromaticity diagram. The solid triangle encompasses all the colours which the system can reproduce. The lengths of the arrowed lines are ten times the average clinical colour contrast thresholds.

I claim:

1. An apparatus for use in diagnosis of field defects comprising:
   an image generator for generating an image comprising an annulus on a background, the annulus having an interruption in a selectable manner and being distinguishable from said background by a distinction in a visually perceivable property;
   means, connected to said image generator, for changing the distinction between said annulus and said background in a graded manner in that property; and
   means, connected to said image generator, for displaying said image.

2. An apparatus according to claim 1 wherein:
   said property is color and the annulus and background are of a first and a second colour respectively and said first and second colors have equal perceived luminosity.

3. An apparatus according to claim 1 or 2 wherein:
   said annulus has no acute angels.

4. An apparatus according to claim 1 or 2 wherein:
   said image further comprises a fixation point at the center of said annulus.

5. An apparatus according to claim 1 or 2 further comprising:
   means for filtering said image to remove any sharp lines from the displayed image.

6. An apparatus according to claim 1 or 2 wherein:
   said means for displaying said image also causes said image to vanish periodically for a predetermined interval.

7. An apparatus according to claim 2 further comprising:
   means for varying the separation in color space between said first color and said second color.

8. An apparatus according to claim 7 further comprising:
   input means for inputting a patient's guess as to the location of the interruption in the annulus; and
   control means for comparing the patient's guess to the actual location of the interruption and controlling the tonal contrast between the first and second colors dependent on the result of the comparison.

9. A method of diagnosing glaucomatous field defects in humans comprising the steps:
   generating an image comprising an annulus on a background, the annulus having an interruption in a selectable manner, and being distinguished form said background by a distinction in a visually perceivable property;
   displaying said image to a patient;
   determining whether said patient can correctly determine the position of the interruption;
   changing said distinction between said annulus and said background in a graded manner in said property;
   repeating the steps of generating and displaying said image; and
   determining whether said patient can detect said interruption to determine the sensitivity of said patient to said property.

10. A method according to claim 9 wherein:
    said property is color, said annulus and background are of first and second colors respectively and said first and second colors have equal perceived luminosity.

11. A method according to claim 9 or 10 wherein:
    said annulus has no acute angles.

12. A method according to claim 9 or 10 wherein said image further comprises:
    a fixation point approximately at the center of said annulus.

13. A method according to claim 9 or 10 further comprising:
    filtering said image to remove any sharp boundaries before said steps of generating and displaying said image.

* * * * *